(12) United States Patent
Tyle et al.

(10) Patent No.: US 8,173,640 B1
(45) Date of Patent: *May 8, 2012

(54) COMPOSITIONS AND METHODS FOR TREATING, REDUCING, AMELIORATING, OR PREVENTING INFECTIONS

(75) Inventors: Praveen Tyle, Pittsford, NY (US); Erning Xia, Penfield, NY (US); Honga Wang, Fairport, NY (US); Susan E. Norton, Rochester, NY (US); Pramod Kumar Gupta, Pittsford, NY (US); Keith W. Ward, Ontario, NY (US); Lynne Brunner, Penfield, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 1037 days.

This patent is subject to a terminal disclaimer.

(21) Appl. No.: 12/115,914

(22) Filed: May 6, 2008

Related U.S. Application Data

(60) Provisional application No. 60/938,765, filed on May 18, 2007.

(51) Int. Cl.
*A61K 31/55* (2006.01)
*A61K 39/40* (2006.01)
*C07D 243/08* (2006.01)

(52) U.S. Cl. ........ 514/218; 540/492; 540/544; 540/575; 540/597; 427/87; 427/85.8

(58) Field of Classification Search ........................ None
See application file for complete search history.

(56) References Cited

U.S. PATENT DOCUMENTS

| | | | | |
|---|---|---|---|---|
| 5,385,900 | A | * | 1/1995 | Konno et al. .................. 514/218 |
| 2002/0187193 | A1 | * | 12/2002 | Roy et al. ...................... 424/486 |

OTHER PUBLICATIONS

Dhople et al., In vitro activity of KRM-1648, either singly or in combination with ofloxacin, against *Mycobacterium ulcerans*, Int. J. of Antimicrobial Agents 17 (2001) 57-16.*
Bassetti et al., Efficacy of the combination of levofloxacin plus ceftazidime in the treatment of hospital-acquired pneumonia in the Intensive Care Units, Int. J. of Antimicrobial Agents 28 (2006) 582-585.*
Bohigian et al., Ocular microbiology and laboratory evaluation, Handbook of Ocular Infections, Inflammation, and External Diseases, Chapter 2, 2000, pp. 11-30.*
U.S. Appl. No. 11/675,930, filed Feb. 2007, Venkatesh et al.*
U.S. Appl. No. 12/604,422, filed Oct. 2009, Tyle et al.*
U.S. Appl. No. 12/051,289, filed Mar. 2008, Tyle et al.*

Brunner et al., "P1679 in vitro activity of SS734, a novel fluoroquinolone, against pathogens associated with bacterial conjunctivitis," Intl J of Antimicrobial Agents, (vol. 29), (p. S475-S476), (Mar. 1, 2007).
Brunner et al., "P1680 Bactericidal activity of SS734, a novel fluoroquinolone, against pathogens associated with bacterial conjunctivitis," Intl J of Antimicrobial Agents, (vol. 29), (p. S476), (Mar. 1, 2007).
Cambau et al., "P1665 Mode of action and resistance of the new fluoroquinolone BOL-303224-A," Intl J of Antimicrobial Agents, (vol. 29), (p. S471), (Mar. 1, 2007).
Dhople et al., "In vitro activity of KRM-1648, either singly or in combination with ofloxacin, against *Mycobacterium ulcerans*," Intl J of Antimicrobial Agents, (vol. 17), (Issue. 1), (p. 57-61), (Jan. 1, 2001).
Bassetti et al., "Efficacy of the combination of levofloxacin plus ceftazidime in the treatment of hospital-acquired pneumonia in the intensive care unit," Intl J of Antimicrobial Agents, (vol. 28), (Issue. 6), (p. 582-585), (Nov. 22, 2006).
Kirchner, "Respiratory synctytial virus: a cause of acute otitis media," Amer Family Phys, (Apr. 15, 1999).
Heikkinen et al., "Importance of respiratory viruses in acute otitis media," Clin Microbiol Reviews, Apr. 2003, (vol. 16), (Issue. 2), (p. 230-241).
Sander, "Otitis externa: a practical guide to treatment and prevention," Amer Family Phys, (vol. 63), (Issue. 5), (p. 927-936), (Mar. 1, 2001).
Sinusitis, "," (Feb. 20, 2007).
Ellison et al., "Report of the first case of invasive fungal sinusitis caused by *Scopulariopsis acremonium*," Arch Otolaryngol Head Neck Surg, Sep. 1998, (vol. 124), (p. 1014-1016).
Jacobs et al., "Prevalence of antimicrobial-resistant pathogens in middle ear fluid: multinational study of 917 children with acute otitis media," Antimicrobial Agents and Chemotherapy, Mar. 1998, (vol. 42), (Issue. 3), (p. 589-595).
Basak et al., "Epidemiological and microbiological diagnosis of suppurative keratitis in Gangetic West Bengal, Eastern India," Indian J Ophthalmol, 2005, (vol. 53), (p. 17-22).
Bharathi et al., "Microbiological diagnosis of infective keratitis: comparative evaluation of direct microscopy and culture results," Br J Ophthalmol, 2006, (vol. 90), (p. 1271-1276).
Bohigian et al., "Ocular microbiology and laboratory evaluation," Handbook of Ocular Infections, Inflammation, and External Diseases, Chapter 2, 2000, (p. 11-30).

* cited by examiner

*Primary Examiner* — Sreeni Padmanabhan
*Assistant Examiner* — Svetlana M Ivanova
(74) *Attorney, Agent, or Firm* — Toan P. Vo

(57) ABSTRACT

Compositions for treating, reducing, ameliorating, or preventing infections comprise a fluoroquinolone having Formulae I-VIII and an additional anti-infective agent. Methods for treating, reducing, ameliorating, or preventing such infection use such compositions. Such compositions and methods can be effective against mixed types of pathogens including certain antibiotic-resistant microbial pathogens found in such infections.

8 Claims, No Drawings

COMPOSITIONS AND METHODS FOR TREATING, REDUCING, AMELIORATING, OR PREVENTING INFECTIONS

CROSS REFERENCE

This application claims the benefit of Provisional Patent Application No. 60/938,765 filed May 18, 2007 which is incorporated by reference herein.

BACKGROUND OF THE INVENTION

The present invention relates to compositions and methods for treating, reducing, ameliorating, or preventing infections. In particular, the present invention relates to such compositions comprising a quinolone carboxylic acid or a derivative thereof, and an additional anti-infective medicament; and to methods of using such compositions. More particularly, the present invention relates to such compositions comprising a fluoroquinolone carboxylic acid or a derivative thereof, and an additional anti-infective medicament; and to methods of using such compositions.

Pathogens continue to pose a serious threat to public health as indicated by a worldwide resurgence of diseases caused by bacteria, fungi, and/or viruses. Infections by pathogenic microorganisms affect a large number of patients every year. Common infections include those of the ear, respiratory system, and eye. An experienced medical practitioner often can determine the etiology of an infection and, therefore, prescribe an effective treatment. However, infections are often caused by mixed types of microorganisms that may not be immediately obvious on presentation. Consequently, an initial treatment regimen may not be immediately effective and must be replaced with another. In cases where the patients are especially vulnerable, such as those with a compromised immune system, a delayed onset of a beneficial effect of the treatment may lead to increased risk of more serious complications.

Otitis media, an infection of the middle ear, is a major worldwide infection in children. By the age of 2 years, seventy percent of children have experienced at least one episode of acute otitis media ("AOM"). T. Heikkinen et al., *Clin. Microbiol. Rev.*, Vol. 16, No. 2, 230 (2003). Otitis media can also occur in adults. AOM is generally considered a bacterial infection that is treated with antibiotics. The three most common bacteria isolated from the middle ear fluid ("MEF") are *Streptococcus pneumoniae, Haemophilus influenzae*, and *Moraxella catarrhalis*. See; e.g., J. T. Kirchener, *American Family Physician*, Apr. 15, 1999. However, since the 1980s, viruses have also been detected in the MEF of children with AOM in approximately twenty percent of the cases. T. Heikkinen et al., supra. The common respiratory viruses such as human rhinovirus, respiratory syncytial virus, influenza viruses, and coronavirus, have been found in children MEF. In addition, in a recent study, fungal DNA was detected in MEF of some patients with recurrent AOM and serous otitis media.

In cases of otitis externa, an infection of the external ear canal, mixed bacteria and fungi have often been found. *Pseudomonas aeruginosa* and *Staphylococcus aureus* are the most common bacteria species, and *Aspergillus* and *Candida* fungus species account for over ninety percent of the cases in which fungi are present. However, fungus is occasionally the primary pathogen in otitis externa, especially in the presence of moisture and heat. R. Sander, *American Family Physician*, Vol. 63, No. 5, 927 (2001).

Infections of the upper respiratory system are also common. The common cold is mostly of viral etiology. However, bacteria and fungi have also often caused other infections of the upper respiratory system. Bacteria are the most common infectious agents in sinusitis. *Streptococcus pneumoniae, Haemophilus influenzae*, and *Moraxella catarrhalis* have been found in most of cases of sinusitis. Other possible bacterial culprits include other streptococcal strains and *Staphylococcus aureus*. While fungi are an uncommon cause of sinusitis, the incidence of such infections is increasing. The most common fungi involved in sinusitis are *Aspergillus* species; in particular, *Aspergillus fumigatus*. Other fungi that can cause sinusitis include *Curvularia* (in particular, *Curvularia lunata*), *Bipolaris, Exserohilum*, and *Mucomycosis*. See, Sinusitis, at http://adam.about.com (visited on Feb. 20, 2007). While fungal sinusitis is mostly non-invasive and does not lead to serious complications, rare cases of invasive fungal sinusitis caused by the fungus *Scopulariopsis acremonium* have been reported. Invasive fungal sinusitis is potentially fatal for immunocompromised patients. M. D. Ellison et al., *Arch. Otolaryngol. Head Neck Surg.*, Vol. 124, 1014 (1998). It can lead to tissue invasion and destruction of adjacent structures (e.g., orbit, central nervous system). Therefore, early detection and treatment are vital for these patients.

Keratitis and conjunctivitis, two common ocular infections, are caused mostly by bacteria, fungi, and/or viruses. Numerous cocci (*Staphylococcus, Streptococcus*, and *Neisseria* species) and bacilli (*Corynebacterium, Propionobacterium, Clostridium, Pseudomonas, Klebsiella, Hemophilus, Moraxella, Proteus, Serratia, Escherichia*, and *Enterobacter* species) have been isolated from cases of ocular infections. Among the fungi causing ocular infections are *Aspergillus, Fusarium*, and *Candida* species. Herpes simplex virus ("HSV"), *Varicella zoster* virus, *Andenovirus*, and *Molluscum contagiosum* have been found in cases of viral ocular infections. See; e.g., G. M. Bohigian and Shailaja Valluri, in *Handbook of Ocular Infections, Inflammation, and External Diseases*, Chapter 2. Moreover, several studies have identified mixed microorganism types in ocular infections, such as mixtures of bacteria and HSV, bacteria and *Andenovirus*, or bacteria and fungi. See; e.g., M. J. Bharathi et al., *Br. J. Ophthalmol.*, 90, 1271 (2006); S. K. Basak, *Indian J. Ophthalmol.*, Vol. 53, No. 1, 17 (2005).

An additional challenge in the treatment of infections is the emergence of bacterial resistance to antibiotics. Such resistance may be attributed to prior widespread, and largely effective, therapeutic and prophylactic use of antibiotics, which, unfortunately, over time has also selected for resistant strains of various bacterial pathogens. Of particular concern to the public health have been the emergence and proliferation of bacterial strains that are resistant to multiple antibiotics in the current arsenal of antimicrobial agents. Therefore, a condition may not respond to an initially prescribed therapy, and, in such a case, another medicament must be given, resulting in delayed control of the pathogen.

Therefore, there is a continued need to develop improved pharmaceutical compositions that can begin to provide benefits to patients in combating infections that do not have clear etiology, soon after being administered to the patients. It is also very desirable to provide pharmaceutical compositions that minimize the risk of complications of the primary infection due to the delayed onset of effectiveness of the treatment.

SUMMARY OF THE INVENTION

In general, the present invention provides pharmaceutical compositions and methods using such compositions for the treatment, reduction, amelioration, or prevention of infections.

In one aspect, the present invention provides pharmaceutical compositions and methods using such compositions for the treatment, reduction, amelioration, or prevention of infections of an eye, an ear, a portion of a respiratory system, or a combination thereof.

In another aspect, an etiology of such infections is not readily ascertainable upon presentation.

In still another aspect, such infections are caused by mixed types of microorganisms.

In still another aspect, such compositions comprise: (a) at least one member of a family of fluoroquinolones that have Formula I or salts thereof; and an additional anti-infective medicament; wherein

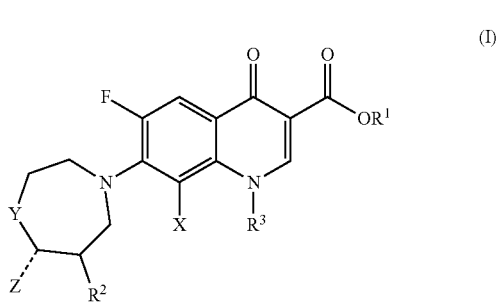

(I)

wherein $R^1$ is selected from the group consisting of hydrogen, unsubstituted lower alkyl groups, substituted lower alkyl groups, cycloalkyl groups, unsubstituted $C_5$-$C_{24}$ aryl groups, substituted $C_5$-$C_{24}$ aryl groups, unsubstituted $C_5$-$C_{24}$ heteroaryl groups, substituted $C_5$-$C_{24}$ heteroaryl groups, and groups that can be hydrolyzed in living bodies; $R^2$ is selected from the group consisting of hydrogen, unsubstituted amino group, and amino groups substituted with one or two lower alkyl groups; $R^3$ is selected from the group consisting of hydrogen, unsubstituted lower alkyl groups, substituted lower alkyl groups, cycloalkyl groups, unsubstituted lower alkoxy groups, substituted lower alkoxy groups, unsubstituted $C_5$-$C_{24}$ aryl groups, substituted $C_5$-$C_{24}$ aryl groups, unsubstituted $C_5$-$C_{24}$ heteroaryl groups, substituted $C_5$-$C_{24}$ heteroaryl groups, unsubstituted $C_5$-$C_{24}$ aryloxy groups, substituted $C_5$-$C_{24}$ aryloxy groups, unsubstituted $C_5$-$C_{24}$ heteroaryloxy groups, substituted $C_5$-$C_{24}$ heteroaryloxy groups, and groups that can be hydrolyzed in living bodies; X is selected from the group consisting of halogen atoms; Y is selected from the group consisting of $CH_2$, O, S, SO, $SO_2$, and $NR^4$, wherein $R^4$ is selected from the group consisting of hydrogen, unsubstituted lower alkyl groups, substituted lower alkyl groups, and cycloalkyl groups; and Z is selected from the group consisting of oxygen and two hydrogen atoms; and wherein the compositions are capable of inhibiting a growth or survival of mixed types of microorganisms causing said infections.

In still another aspect, said additional anti-infective medicament comprises a quinolone other than those represented by Formula I.

In still another aspect, said additional anti-infective medicament comprises a quinolone other than those represented by Formula I, and another agent selected from the group consisting of antiviral agents, antifungal agents, antiprotozoal agents, and combinations thereof.

In yet another aspect, said additional anti-infective medicament is selected from the group consisting of antifungal agents, antiviral agents, and combinations thereof.

In a further aspect, a composition of the present invention comprises a single enantiomer of a compound having Formula I, and an additional anti-infective medicament.

In still another aspect, a composition of the present invention comprises: (a) a member of a family of fluoroquinolones having Formula II or salts thereof; and (b) an additional anti-infective medicament; wherein

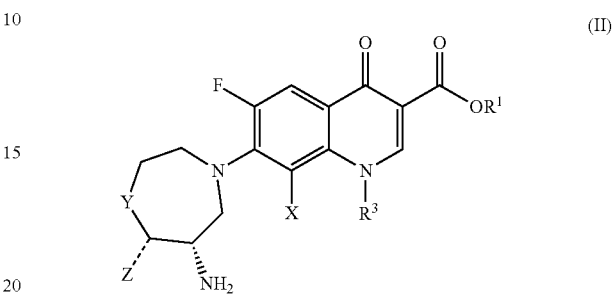

(II)

wherein $R^3$, X, Y, and Z have the meanings as disclosed above; and wherein the composition is capable of inhibiting a growth or survival of mixed types of microorganisms causing an infection.

In still another aspect, the present invention provides a method for treating, reducing, ameliorating, or preventing an infection of an ear, a portion of a respiratory system, an eye, or a combination thereof. The method comprises administering a composition comprising: (a) a fluoroquinolone having Formula I or II; and (b) an additional anti-infective medicament, to a site of infection to treat, reduce, or ameliorate said infection.

In one embodiment, the method comprises topically administering such a composition. In another embodiment, the method comprises orally administering such a composition.

In yet another aspect, said infection comprises infections of an ear, a portion of an upper respiratory system, an eye, or a combination thereof.

Other features and advantages of the present invention will become apparent from the following detailed description and claims.

DETAILED DESCRIPTION

As used herein, the term "lower alkyl" or "lower alkyl group" means a $C_1$-$C_{15}$ linear- or branched-chain saturated aliphatic hydrocarbon monovalent group, which may be unsubstituted or substituted. The group may be partially or completely substituted with halogen atoms (F, Cl, Br, or I). Non-limiting examples of lower alkyl groups include methyl, ethyl, n-propyl, 1-methylethyl (or isopropyl), n-butyl, n-pentyl, 1,1-dimethylethyl (or t-butyl), and the like. It may be abbreviated as "Alk".

As used herein, the term "lower alkoxy" or "lower alkoxy group" means a $C_1$-$C_{15}$ linear- or branched-chain saturated aliphatic alkoxy monovalent group, which may be unsubstituted or substituted. The group may be partially or completely substituted with halogen atoms (F, Cl, Br, or I). Non-limiting examples of lower alkoxy groups include methoxy, ethoxy, n-propoxy, 1-methylethoxy(isopropoxy), n-butoxy, n-pentoxy, t-butoxy, and the like.

The term "cycloalkyl" or "cycloalkyl group" means a stable aliphatic saturated 3- to 15-membered monocyclic or polycyclic monovalent radical consisting solely of carbon and hydrogen atoms which may comprise one or more fused or bridged ring(s), preferably a 3- to 7-membered monocyclic rings. Other exemplary embodiments of cycloalkyl groups include 7- to 10-membered bicyclic rings. Unless otherwise specified, the cycloalkyl ring may be attached at any carbon atom which results in a stable structure and, if substituted, may be substituted at any suitable carbon atom which results in a stable structure. Exemplary cycloalkyl groups include cyclopropyl, cyclobutyl, cyclopentyl, cyclohexyl, cycloheptyl, cyclooctyl, cyclononyl, cyclodecyl, norbornyl, adamantyl, tetrahydronaphthyl(tetralin), 1-decalinyl, bicyclo[2.2.2]octanyl, 1-methylcyclopropyl, 2-methylcyclopentyl, 2-methylcyclooctyl, and the like.

As used herein, the term "aryl" or "aryl group" means an aromatic carbocyclic monovalent or divalent radical. In some embodiments, the aryl group has a number of carbon atoms from 5 to 24 and has a single ring (e.g., phenyl or phenylene), multiple condensed rings (e.g., naphthyl or anthranyl), or multiple bridged rings (e.g., biphenyl). Unless otherwise specified, the aryl ring may be attached at any suitable carbon atom which results in a stable structure and, if substituted, may be substituted at any suitable carbon atom which results in a stable structure. Non-limiting examples of aryl groups include phenyl, naphthyl, anthryl, phenanthryl, indanyl, indenyl, biphenyl, and the like. It may be abbreviated as "Ar".

The term "heteroaryl" or "heteroaryl group" means a stable aromatic monocyclic or polycyclic monovalent or divalent radical, which may comprise one or more fused or bridged ring(s). In some embodiments, the heteroaryl group has 5-24 members, preferably a 5- to 7-membered monocyclic or 7- to 10-membered bicyclic radical. The heteroaryl group can have from one to four heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Non-limiting examples of heteroaryls include furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, triazinyl, indolizinyl, azaindolizinyl, indolyl, azaindolyl, diazaindolyl, dihydroindolyl, dihydroazaindoyl, isoindolyl, azaisoindolyl, benzofuranyl, furanopyridinyl, furanopyrimidinyl, furanopyrazinyl, furanopyridazinyl, dihydrobenzofuranyl, dihydrofuranopyridinyl, dihydrofuranopyrimidinyl, benzothienyl, thienopyridinyl, thienopyrimidinyl, thienopyrazinyl, thienopyridazinyl, dihydrobenzothienyl, dihydrothienopyridinyl, dihydrothienopyrimidinyl, indazolyl, azaindazolyl, diazaindazolyl, benzimidazolyl, imidazopyridinyl, benzthiazolyl, thiazolopyridinyl, thiazolopyrimidinyl, benzoxazolyl, benzoxazinyl, benzoxazinonyl, oxazolopyridinyl, oxazolopyrimidinyl, benzisoxazolyl, purinyl, chromanyl, azachromanyl, quinolizinyl, quinolinyl, dihydroquinolinyl, tetrahydroquinolinyl, isoquinolinyl, dihydroisoquinolinyl, tetrahydroisoquinolinyl, cinnolinyl, azacinnolinyl, phthalazinyl, azaphthalazinyl, quinazolinyl, azaquinazolinyl, quinoxalinyl, azaquinoxalinyl, naphthyridinyl, dihydronaphthyridinyl, tetrahydronaphthyridinyl, pteridinyl, carbazolyl, acridinyl, phenazinyl, phenothiazinyl, and phenoxazinyl, and the like.

In general, the present invention provides a pharmaceutical composition and a method for treating, reducing, or ameliorating an infection.

In one aspect, said infection has an etiology that is not readily ascertainable upon presentation.

In another aspect, said infection is caused by mixed types of microorganisms.

In still another aspect, said infection comprises an infection of an ear, a portion of a respiratory system, an eye, or a combination thereof.

In one aspect, said infection is selected from the group consisting of otitis, sinusitis, nasophrayngitis, orophrayngitis, epiglottitis, laryngotracheitis, bronchitis, bronchiolitis, pneumonia, keratitis, conjunctivitis, blepharitis, hordeolum, phlyctenulosis, endophthalmitis, preseptal and orbital cellulites, dacryocystitis, and combinations thereof.

In another aspect, a composition of the present invention comprises: (a) at least one member of a family of fluoroquinolones that have Formula I or salts thereof; and (b) an additional anti-infective medicament; wherein

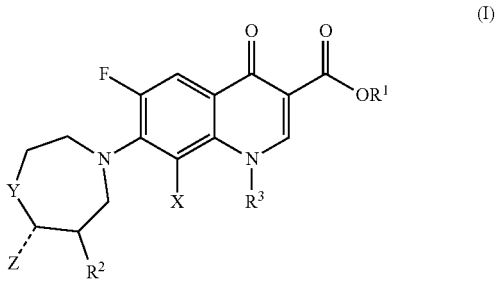

(I)

wherein $R^1$ is selected from the group consisting of hydrogen, unsubstituted lower alkyl groups, substituted lower alkyl groups, cycloalkyl groups, unsubstituted $C_5$-$C_{24}$ aryl groups, substituted $C_5$-$C_{24}$ aryl groups, unsubstituted $C_5$-$C_{24}$ heteroaryl groups, substituted $C_5$-$C_{24}$ heteroaryl groups, and groups that can be hydrolyzed in living bodies; $R^2$ is selected from the group consisting of hydrogen, unsubstituted amino group, and amino groups substituted with one or two lower alkyl groups; $R^3$ is selected from the group consisting of hydrogen, unsubstituted lower alkyl groups, substituted lower alkyl groups, cycloalkyl groups, unsubstituted lower alkoxy groups, substituted lower alkoxy groups, unsubstituted $C_5$-$C_{24}$ aryl groups, substituted $C_5$-$C_{24}$ aryl groups, unsubstituted $C_5$-$C_{24}$ heteroaryl groups, substituted $C_5$-$C_{24}$ heteroaryl groups, unsubstituted $C_5$-$C_{24}$ aryloxy groups, substituted $C_5$-$C_{24}$ aryloxy groups, unsubstituted $C_5$-$C_{24}$ heteroaryloxy groups, substituted $C_5$-$C_{24}$ heteroaryloxy groups, and groups that can be hydrolyzed in living bodies; X is selected from the group consisting of halogen atoms; Y is selected from the group consisting of $CH_2$, O, S, SO, $SO_2$, and $NR^4$, wherein $R^4$ is selected from the group consisting of hydrogen, unsubstituted lower alkyl groups, substituted lower alkyl groups, and cycloalkyl groups; and Z is selected from the group consisting of oxygen and two hydrogen atoms; and wherein the composition is capable of inhibiting a growth or survival of mixed types of microorganisms causing said infection.

In one aspect, $R^1$ is selected from the group consisting of hydrogen, $C_1$-$C_5$ (or alternatively, $C_1$-$C_3$) substituted and unsubstituted alkyl groups, $C_3$-$C_{10}$ (or alternatively, $C_3$-$C_5$) cycloalkyl groups, $C_5$-$C_{14}$ (or alternatively, $C_6$-$C_{14}$, or $C_5$-$C_{10}$, or $C_6$-$C_{10}$) substituted and unsubstituted aryl groups, $C_5$-$C_{14}$ (or alternatively, $C_6$-$C_{14}$, or $C_5$-$C_{10}$, or $C_6$-$C_{10}$) substituted and unsubstituted heteroaryl groups, and groups that can be hydrolyzed in living bodies. In one embodiment, $R^1$ is selected from the group consisting of $C_1$-$C_5$ (or alternatively, $C_1$-$C_3$) substituted and unsubstituted alkyl groups.

In another aspect, $R^2$ is selected from the group consisting of unsubstituted amino group and amino groups substituted with one or two $C_1$-$C_5$ (or alternatively, $C_1$-$C_3$) alkyl groups.

In still another aspect, $R^3$ is selected from the group consisting of hydrogen, $C_1$-$C_5$ (or alternatively, $C_1$-$C_3$) substituted and unsubstituted alkyl groups, $C_3$-$C_{10}$ (or alternatively, $C_3$-$C_5$) cycloalkyl groups, $C_1$-$C_5$ (or alternatively, $C_1$-$C_3$) substituted and unsubstituted alkoxy groups, $C_5$-$C_{14}$ (or alternatively, $C_6$-$C_{14}$, or $C_5$-$C_{10}$, or $C_6$-$C_{10}$) substituted and unsubstituted aryl groups, $C_5$-$C_{14}$ (or alternatively, $C_6$-$C_{14}$, or $C_5$-$C_{10}$, or $C_6$-$C_{10}$) substituted and unsubstituted heteroaryl groups, and $C_5$-$C_{14}$ (or alternatively, $C_6$-$C_{14}$, or $C_5$-$C_{10}$, or $C_6$-$C_{10}$) substituted and unsubstituted aryloxy groups. In one embodiment, $R^3$ is selected from the group consisting of $C_3$-$C_{10}$ (or alternatively, $C_3$-$C_5$) cycloalkyl groups.

In yet another aspect, X is selected from the group consisting of Cl, F, and Br. In one embodiment, X is Cl. In another embodiment, X is F.

In a further aspect, Y is $CH_2$ and Z comprises two hydrogen atoms.

In still another aspect, Y is NH, Z is O, and X is Cl.

Some non-limiting members of the family of compounds having Formula I are shown in Table 1. Other compounds of the family not listed in Table 1 are also suitable in selected situations.

TABLE 1

Some Selected Fluoroquinolones

| Compound | $R^1$ | $R^2$ | $R^3$ | X | Y | Z |
|---|---|---|---|---|---|---|
| 1 | H | H | $CH_3$ | Cl | $CH_2$ | 2 H |
| 2 | H | $NH_2$ | $CH_3$ | Cl | $CH_2$ | 2 H |
| 3 | H | $NH_2$ | cyclopropyl | Cl | $CH_2$ | 2 H |
| 4 | H | $NH(CH_3)$ | cyclopropyl | Cl | $CH_2$ | 2 H |
| 5 | H | $N(CH_3)_2$ | cyclopropyl | Cl | $CH_2$ | 2 H |
| 6 | $CH_3$ | $NH_2$ | cyclopropyl | Cl | $CH_2$ | 2 H |
| 7 | $C_2H_5$ | $NH_2$ | cyclopropyl | Cl | $CH_2$ | 2 H |
| 8 | H | $NH_2$ | cyclopropyl | F | $CH_2$ | 2 H |
| 9 | H | $NH_2$ | cyclopropyl | Br | $CH_2$ | 2 H |
| 10 | H | $NH(C_3H_5)$ | cyclopropyl | Cl | $CH_2$ | 2 H |
| 11 | H | $NH(C_3H_5)$ | cyclopropyl | F | $CH_2$ | 2 H |
| 12 | H | $NH_2$ | cyclopropyl | Cl | $CH_2$ | 2 H |
| 13 | H | $NH_2$ | cyclopropyl | Cl | $CH_2$ | O |
| 14 | H | $NH_2$ | cyclopropyl | F | $CH_2$ | O |
| 15 | H | $NH_2$ | cyclopropyl | Br | $CH_2$ | O |
| 16 | H | $NH_2$ | cyclopropyl | Cl | $CH(C_3H_5)$ | O |
| 17 | $CH_3$ | $NH_2$ | cyclopropyl | Cl | $CH_2$ | O |
| 18 | $CH_3$ | $NH(CH_3)$ | cyclopropyl | Cl | $CH_2$ | O |
| 19 | $CH_3$ | $N(CH_3)_2$ | cyclopropyl | Cl | $CH_2$ | O |
| 20 | $CH_3$ | $NH(C_3H_5)$ | cyclopropyl | Cl | $CH_2$ | O |
| 21 | $CH_3$ | $NH(C_3H_5)$ | cyclopropyl | Cl | $CH_2$ | O |
| 22 | $CH_3$ | $N(CH_3)(C_2H_5)$ | cyclopropyl | Cl | $CH_2$ | O |
| 23 | H | $NH_2$ | cyclopropyl | Cl | NH | O |
| 24 | $CH_3$ | $NH(CH_3)$ | cyclopropyl | Cl | NH | O |
| 25 | H | 2H | cyclopropyl | Cl | NH | O |

In one embodiment, the fluoroquinolone carboxylic acid included in a composition of the present invention has Formula III.

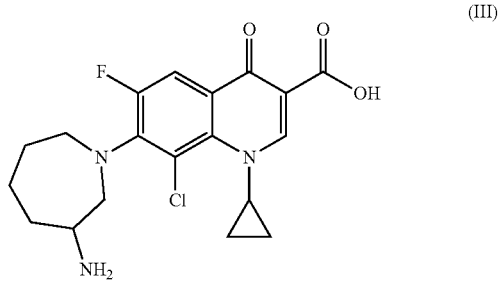

(III)

In another embodiment, the fluoroquinolone carboxylic acid included in a composition of the present invention has Formula IV, V, or VI.

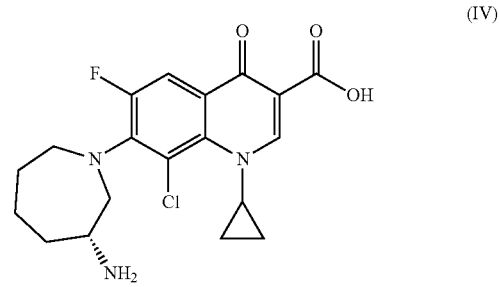

(IV)

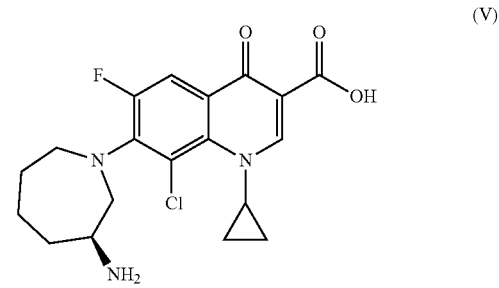

(V)

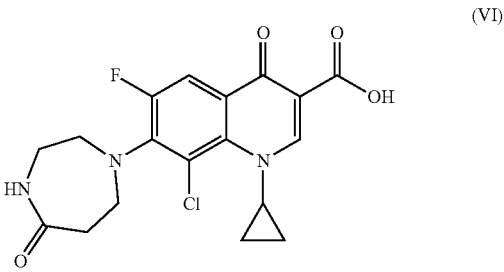

(VI)

In still other embodiments, the fluoroquinolone carboxylic acid included in a composition of the present invention has Formula VII or VIII.

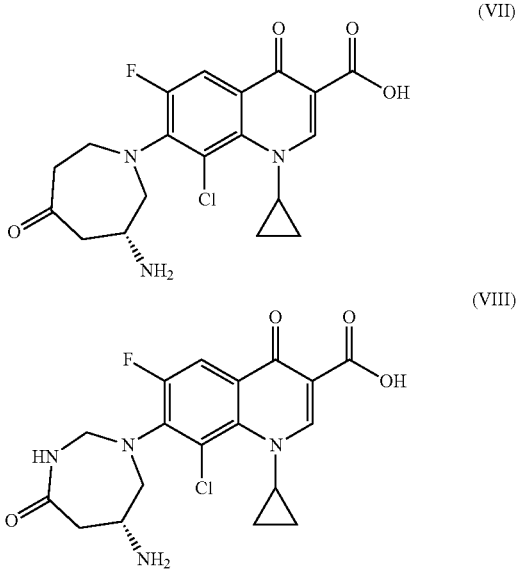

In still another aspect, a composition of the present invention comprises an enantiomer of one of the compounds having Formula I, II, or III.

In still another aspect, a composition of the present invention comprises a mixture of enantiomers of one of the compounds having Formula I, II, or III.

In a further aspect, the additional anti-infective medicament is selected from the group consisting of an antibacterial agent other than the quinolones having Formulae I, II, III, IV, V, VI, VII, and VIII; an antifungal agent; an antiviral agent; an antiprotozoal agent; and combinations thereof.

In another aspect, the additional antibacterial agent other than the quinolones having Formulae I, II, III, IV, V, VI, VII, and VIII comprises another quinolone.

In still another aspect, said another quinolone is selected from the group consisting of cinoxacin, ciprofloxacin, clinafloxacin, difloxacin, enoxacin, fleroxacin, gatifloxacin, grepafloxacin, levofloxacin, lomefloxacin, miloxacin, moxifloxacin, nadifloxacin, norfloxacin, ofloxacin, pazufloxacin, pefloxacin, sitafloxacin, sparfloxacin, temafloxacin, tosufloxacin, trovafloxacin, mixtures thereof, and combinations thereof.

In yet another aspect, said another quinolone has a $MIC_{90}$ value for a Gram-negative bacterium that is lower than that of the fluoroquinolone having Formula I, II, III, IV, V, VI, VII, or VIII for the same bacterium, said fluoroquinolone being included in the composition. $MIC_{90}$ is the minimum concentration of the active compound required to inhibit ninety percent of the growth of a specified pathogen, in μg/ml.

Non-limiting examples of antibacterial agents other than the quinolones having antibacterial agent other than the quinolones having Formulae I, II, III, IV, V, VI, VII, and VIII include biologically-derived antibacterial agents such as aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), β-lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefinenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefinetazole, cefininox, cefotetan, cefoxitin), monobactams (e.g., azheonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin 0, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, ticarcillin), ritipenem, lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), cycloserine, mupirocin, and tuberin.

Non-limiting examples of synthetic antibacterial agents include 2,4-diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, gatifloxacin, grepafloxacin, levofloxacin, lomefloxacin, miloxacin, moxifloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin, sulfonamides (e.g., acetyl sulfamethoxypyrazine, benzylsulfamide, chloramines B, chloramines T, dichloramine T, $n^2$-formylsulfisomidine, $n^4$-β-D-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, $n^4$-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), clofoctol, hexedine, methenamine, methenamine anhydromethylene citrate, methenamine hippurate, methenamine mandelate, methenamine sulfosalicylate, nitroxoline, taurolidine, and xibomol. In one embodiment, a composition of the present invention comprises an anti-infective agent selected from the group consisting of cinoxacin, ciprofloxacin, clinafloxacin, difloxacin, enoxacin, fleroxacin, flumequine, gatifloxacin, grepafloxacin, levofloxacin, lomefloxacin, miloxacin, moxifloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, and trovafloxacin.

Non-limiting examples of antiviral agents include rifampin, ribavirin, pleconaryl, cidofovir, acyclovir, pencyclovir, gancyclovir, valacyclovir, famciclovir, foscarnet, vidarabine, amantadine, zanamivir, oseltamivir, resquimod, adenosine arabinoside, cytosine arabinoside, antiproteases, PEGylated interferon (Pegasys™), anti HIV proteases (e.g. lopinivir, saquinivir, amprenavir, HIV fusion inhibitors, nucleotide HIV RT inhibitors (e.g., AZT, lamivudine, abacavir), non-nucleotide HIV RT inhibitors, doconosol, interferons, butylated hydroxytoluene (BHT), and hypericin.

Non-limiting examples of biologically-derived antifungal agents include polyenes (e.g., amphotericin B, candicidin, dermostatin, filipin, fungichromin, hachimycin, hamycin, lucensomycin, mepartricin, natamycin, nystatin, pecilocin, perimycin), azaserine, griseofulvin, oligomycins, neomycin undecylenate, pyrrolnitrin, siccanin, tubercidin, and viridin.

Non-limiting examples of synthetic antifungal agents include allylamines (e.g., butenafine, naftifine, terbinafine), imidazoles (e.g., bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole), acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, and zinc propionate.

Non-limiting examples of antiprotozoal agents include polymycin B sulfate, bacitracin zinc, neomycine sulfate (e.g., Neosporin®), imidazoles (e.g., clotrimazole, miconazole, ketoconazole), aromatic diamidines (e.g., propamidine isethionate, brolene), polyhexamethylene biguanide ("PHMB"), chlorhexidine, pyrimethamine (Daraprim®), sulfadiazine, folinic acid (leucovorin), clindamycin, and trimethoprim-sulfamethoxazole.

The amount of a fluoroquinolone compound having Formula I, II, III, IV, V, VI, VII, or VIII that is incorporated into a composition of the present invention is not critical; the concentration should be within a range sufficient to permit ready application of the composition to the affected tissue area in an amount which will deliver the desired amount of compound to the desired treatment site and to provide the desired therapeutic effect. In some embodiments of the present invention, compositions comprise a fluoroquinolone having Formula I, II, III, IV, V, VI, VII, or VIII in a concentration in a range from about 0.0001% to 10% by weight (or alternatively, from about 0.001% to about 5%, or from about 0.01% to about 5%, or from about 0.01% to about 2%, or from about 0.01% to about 1%, or from about 0.01% to about 0.7%, or from about 0.01% to about 0.5%, by weight).

In another aspect, the concentration of said additional anti-infective medicament in a composition of the present invention can be in the range from about 0.0001% to 10% by weight (or alternatively, from about 0.001% to about 5%, or from about 0.01% to about 5%, or from about 0.01% to about 2%, or from about 0.01% to about 1%, or from about 0.01% to about 0.7%, or from about 0.01% to about 0.5%, by weight).

In still another aspect, a composition of the present invention further comprises a pharmaceutically acceptable carrier.

A fluoroquinolone compound and an additional anti-infective medicament that are disclosed herein can be formulated into a pharmaceutical composition for topical, oral, or systemic administration for the treatment, reduction, amelioration, or prevention of an. In an embodiment, such infection comprises an infection of an ear, a portion of a respiratory system, an eye, or a combination thereof. Such a composition comprises a fluoroquinolone compound having Formula I, II, III, IV, V, VI, VII, or VIII, an additional anti-infective medicament, and a pharmaceutically acceptable carrier for the administration, which carrier can be determined by a person having skill in the art of pharmaceutical formulation for the applications disclosed above. For example, various pharmaceutically acceptable carriers known in the art can be used to formulate a solution, suspension, dispersion, ointment, gel, capsule, or tablet. A fluoroquinolone compound having Formula I, II, III, IV, V, VI, VII, or VIII disclosed herein is particularly suitable for a treatment, reduction, amelioration, or prevention of infections of an ear, a portion of a respiratory system, an eye, or a combination thereof, which infections are caused by bacteria, fungi, viruses, protozoans, or combinations thereof, including, but not being limited to, the bacteria, fungi, viruses, and protozoans disclosed above. In one embodiment, such infections are caused by mixed microorganisms comprising at least one bacterium. In another embodiment, such a fluoroquinolone and an additional anti-infective medicament or agent are formulated into a solution, ointment, suspension, dispersion, or gel.

In one embodiment, a topical composition of the present invention comprises an aqueous solution or suspension. Typically, purified or deionized water is used. The pH of the composition is adjusted by adding any physiologically and otically acceptable pH adjusting acids, bases, or buffers to within the range of about 3 to about 8.5 (or alternatively, or from about 4 to about 7.5, or from about 4 to about 6.5, or from about 5 to about 6.5). Examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, THAM (trishydroxymethylamino-methane), and the like. Salts and buffers include citrate/dextrose, sodium bicarbonate, ammonium chloride and mixtures of the aforementioned acids and bases. pH buffers are introduced into the composition to maintain a stable pH and to improve product tolerance by the user. In some embodiments, the pH is in the range from about 4 to about 7.5. Biological buffers for various pHs are available, for example, from Sigma-Aldrich. A composition of the present invention can have a viscosity in the range from about 5 to about 100,000 centipoise ("cp") or mPa·s (or alternatively, from about 10 to about 50,000, or from about 10 to about 20,000, or from about 10 to about 10,000, or from about 10 to about 1,000, or from about 100 to about 10,000, or from about 100 to about 20,000, or from about 100 to about 50,000 or from about 500 to about 10,000, or from about 500 to about 20,000 cp).

In another embodiment, a topical composition of the present invention comprises an ointment, emulsion or cream (such as oil-in-water emulsion), or gel.

Ointments generally are prepared using either (1) an oleaginous base; i.e., one consisting of fixed oils or hydrocarbons, such as white petrolatum or mineral oil, or (2) an absorbent base; i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate, hydrophilic colloids, such as acacia colloidal clays, veegum, and the like. Upon formation of the emulsion, the active ingredient (compound) customarily is added in an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compound) is added to the formulation at the desired concentration at a point preceding addition of the gelling agent.

Moreover, a topical composition of the present invention can contain one or more of the following: preservatives, surfactants, adjuvants including additional medicaments, antioxidants, tonicity adjusters, viscosity modifiers, and the like.

Preservatives may be used to inhibit microbial contamination of the product when it is dispensed in single or multidose containers, and can include: quaternary ammonium derivatives, (benzalkonium chloride, benzylammonium chloride, cetylmethyl ammonium bromide, cetylpyridinium chloride), benzethonium chloride, organomercury compounds (Thimerosal, phenylmercury acetate, phenylmercury nitrate), methyl and propyl p-hydroxy-benzoates, betaphenylethyl alcohol, benzyl alcohol, phenylethyl alcohol, phenoxyethanol, and mixtures thereof. These compounds are used at effective concentrations, typically from about 0.005% to about 5% (by weight), depending on the preservative or preservatives selected. The amount of the preservative used should be enough so that the solution is physically stable; i.e., a precipitate is not formed, and antibacterially effective.

The solubility of the components, including a fluoroquinolone having Formula I, II, III, IV, V, VI, VII, or VIII of the present compositions may be enhanced by a surfactant or other appropriate co-solvent in the composition or solubility enhancing agents like cyclodextrins such as hydroxypropyl, hydroxyethyl, glucosyl, maltosyl and maltotriosyl derivatives of $\alpha$-, $\beta$-, and $\gamma$-cyclodextrin. In one embodiment, the composition comprises 0.1% to 20% hydroxypropyl-$\beta$-cyclodextrin; alternatively, 1% to 15% (or 2% to 10%) hydroxypropyl-$\beta$-cyclodextrin. Co-solvents include polysorbates (for example, polysorbate 20, 60, and 80), polyoxyethylene/polyoxypropylene surfactants (e.g., Pluronic® F68, F84, F127, and P103), cyclodextrin, fatty-acid triglycerides, glycerol, polyethylene glycol, other solubility agents such as octoxynol 40 and tyloxapol, or other agents known to those skilled in the art and mixtures thereof. The amount of solubility enhancer used will depend on the amount of fluoroquinolone in the composition, with more solubility enhancer used for greater amounts of fluoroquinlones. Typically, solubility enhancers are employed at a level of from 0.01% to about 20% (alternatively, from about 0.1% to about 10%, from about 0.1% to about 5%, or from about 0.1% to about 2%) by weight depending on the ingredient.

The use of viscosity enhancing agents to provide the compositions of the invention with viscosities greater than the viscosity of simple aqueous solutions may be desirable to increase absorption of the active compounds by the target tissues or to increase the retention time in the ear. Such viscosity enhancing agents include, for example, polyvinyl alcohol, polyvinyl pyrrolidone, methyl cellulose, hydroxypropylmethyl cellulose, hydroxyethyl cellulose, carboxymethyl cellulose, hydroxypropyl cellulose or other agents know to those skilled in the art. Such agents are typically employed at a level of from about 0.01% to about 10% (alternatively, from about 0.1% to about 5%, or from about 0.1% to about 2%) by weight.

Suitable surfactants include polyvinyl pyrolidone, polyvinyl alcholol, polyethylene glycol, ethylene glycol, and propylene glycol. Other surfactants are polysorbates (such as polysorbate 80 (polyoxyethylene sorbitan monooleate), polysorbate 60 (polyoxyethylene sorbitan monostearate), polysorbate 20 (polyoxyethylene sorbitan monolaurate), commonly known by their trade names of Tween® 80, Tween® 60, Tween® 20), poloxamers (synthetic block polymers of ethylene oxide and propylene oxide, such as those commonly known by their trade names of Pluronic®; e.g., Pluronic® F127 or Pluronic® F 108)), or poloxamines (synthetic block polymers of ethylene oxide and propylene oxide attached to ethylene diamine, such as those commonly known by their trade names of Tetronic®; e.g., Tetronic® 1508 or Tetronic® 908, etc., other nonionic surfactants such as Brij®, Myrj®, and long chain fatty alcohols (i.e., oleyl alcohol, stearyl alcohol, myristyl alcohol, docosohexanoyl alcohol, etc.) with carbon chains having about 12 or more carbon atoms (e.g., such as from about 12 to about 24 carbon atoms). The surfactant helps a topical formulation to spread on the surface of narrow passages.

It is often that an infection is followed by inflammation. Therefore, in another aspect, a composition of the present invention further comprises an anti-inflammatory agent. Anti-inflammatory agents include the well-known glucocorticosteroids and the non-steroidal anti-inflammatory drugs ("NSAIDs").

Non-limiting examples of the glucocorticosteroids are: 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, fluclo-
ronide, flumethasone, flunisolide, fluocinolone acetonide,
fluocinonide, fluocortin butyl, fluocortolone, fluo-
rometholone, fluperolone acetate, fluprednidene acetate, flu-
prednisolone, flurandrenolide, fluticasone propionate, for-
mocortal, halcinonide, halobetasol propionate,
halometasone, halopredone acetate, hydrocortarnate, hydro-
cortisone, loteprednol etabonate, mazipredone, medrysone,
meprednisone, methylprednisolone, mometasone furoate,
paramethasone, prednicarbate, prednisolone, prednisolone
25-diethylamino-acetate, prednisolone sodium phosphate,
prednisone, prednival, prednylidene, rimexolone, tixocortol,
triamcinolone, triamcinolone acetonide, triamcinolone bene-
tonide, triamcinolone hexacetonide, their physiologically
acceptable salts, combinations thereof, and mixtures thereof.

The preferred glucocorticoids for otic use include dexam-
ethasone, loteprednol, rimexolone, prednisolone, fluo-
rometholone, hydrocortisone, and their derivatives. The pre-
ferred glucocorticoids for nasal use include mometasone,
fluticasone, beclomethasone, flunisolide, triamcinolone,
budesonide, and their derivatives.

Non-limiting examples of the NSAIDs are: aminoarylcar-
boxylic acid derivatives (e.g., enfenamic acid, etofenamate,
flufenamic acid, isonixin, meclofenamic acid, mefenamic
acid, niflumic acid, talniflumate, terofenamate, tolfenamic
acid), arylacetic acid derivatives (e.g., aceclofenac, acemeta-
cin, alclofenac, amfenac, amtolmetin guacil, bromfenac,
bufexamac, cinmetacin, clopirac, diclofenac sodium, etod-
olac, felbinac, fenclozic acid, fentiazac, glucametacin,
ibufenac, indomethacin, isofezolac, isoxepac, lonazolac,
metiazinic acid, mofezolac, oxametacine, pirazolac, proglu-
metacin, sulindac, tiaramide, tolmetin, tropesin, zomepirac),
arylbutyric acid derivatives (e.g., bumadizon, butibufen, fen-
bufen, xenbucin), arylcarboxylic acids (e.g., clidanac, ketoro-
lac, tinoridine), arylpropionic acid derivatives (e.g., almino-
profen, benoxaprofen, bermoprofen, bucloxic acid,
carprofen, fenoprofen, flunoxaprofen, flurbiprofen, ibupro-
fen, ibuproxam, indoprofen, ketoprofen, loxoprofen,
naproxen, oxaprozin, piketoprolen, pirprofen, pranoprofen,
protizinic acid, suprofen, tiaprofenic acid, ximoprofen, zal-
toprofen), pyrazoles (e.g., difenamizole, epirizole), pyrazo-
lones (e.g., apazone, benzpiperylon, feprazone, mofebuta-
zone, morazone, oxyphenbutazone, phenylbutazone,
pipebuzone, propyphenazone, ramifenazone, suxibuzone,
thiazolinobutazone), salicylic acid derivatives (e.g., acetami-
nosalol, aspirin, benorylate, bromosaligenin, calcium acetyl-
salicylate, diflunisal, etersalate, fendosal, gentisic acid, gly-
col salicylate, imidazole salicylate, lysine acetylsalicylate,
mesalamine, morpholine salicylate, 1-naphthyl salicylate,
olsalazine, parsalmide, phenyl acetylsalicylate, phenyl sali-
cylate, salacetamide, salicylamide o-acetic acid, salicylsulfu-
ric acid, salsalate, sulfasalazine), thiazinecarboxamides (e.g.,
ampiroxicam, droxicam, isoxicam, lornoxicam, piroxicam,
tenoxicam), ε-acetamidocaproic acid, S-(5'-adenosyl)-L-me-
thionine, 3-amino-4-hydroxybutyric acid, amixetrine,
bendazac, benzydamine, α-bisabolol, bucolome, difenpira-
mide, ditazol, emorfazone, fepradinol, guaiazulene, nabume-
tone, nimesulide, oxaceprol, paranyline, perisoxal, proqua-
zone, superoxide dismutase, tenidap, zileuton, their
physiologically acceptable salts, combinations thereof, and
mixtures thereof. In one embodiment, the NSAID is
diclofenac, furbiprofen, or ketorolac.

Other non-steroidal anti-inflammatory agents include the
cyclooxygenase type II selective inhibitors, such as cele-
coxib, and etodolac; platelet activating factor ("PAF")
antagonists, such as apafant, bepafant, minopafant, nupafant,
and modipafant; phosphodiesterase ("PDE") IV inhibitors,
such as ariflo, torbafylline, rolipram, filaminast, piclamilast,
cipamfylline, and roflumilast; inhibitors of cytokine produc-
tion, such as inhibitors of the NF-κB transcription factor; or
other anti-inflammatory agents known to those skilled in the
art.

The concentrations of the anti-inflammatory agents con-
tained in the compositions of the present invention will vary
based on the agent or agents selected and the type of inflam-
mation being treated. The concentrations will be sufficient to
reduce inflammation in the targeted tissues following topical
application of the compositions to those tissues. Such con-
centrations are typically in the range from about 0.0001 to
about 3% by weight (or alternatively, from about 0.01 to about
2%, or from about 0.05% to about 1%, by weight).

Bacterial pathogens that have been isolated from cases of
ear infection include *Pseudomonas aeruginosa, Staphylococ-
cus aureus, Streptococcus pneumoniae, Streptococcus pyro-
genes, Streptococcus faecalis, Haemophilus influenzae,
Moraxella catarahalis, Escherichia coli, Proteus* species,
*Klebsiella* species, and *Enterococcus* species. Several of
these species from the isolates have been found to be resistant
to a number of antimicrobial drugs. For example, a published
study of antimicrobial-resistant pathogens in middle-ear fluid
of children with acute otitis media shows that thirty percent of
the *S. pneumoniae* isolates were intermediately or fully resis-
tant, and eight percent fully resistant, to penicillin; ten percent
of the isolates were resistant to amoxicillin or amoxicillin-
clavulanate. M. R. Jacobs et al., *Antimicrobial Agents and
Chemotherapy*, Vol. 42, No. 3, 589 (1998). The same study
shows that thirty percent of *H. influenzae* isolates produced
β-lactamase, and thus, were expected to be resistant to peni-
cillin.

Bacterial pathogens that have been isolated from cases of
upper respiratory infection include *Staphylococcus aureus,
Staphylococcus epidermidis, Streptococcus pneumoniae,
Streptococcus pyrogenes, Haemophilus influenzae, Pep-
tostreptococcus* species, and *Bacteroides* species. Some of
these strains have been found to be resistant to commonly
used antibiotics, as mentioned above.

Anti-bacterial activity of the compound having Formula IV
was tested against several Gram-negative reference bacteria
strains and compared to the anti-bacterial activity of three
commercially available antibiotics (nadifloxacin, ofloxacin,
and sparfloxacin). The results are shown in Table 2 as $MIC_{90}$
values (minimum concentration of the active compound
required to inhibit ninety percent of the growth of a specified
pathogen, in µg/ml).

TABLE 2

Comparison of In vitro Anti-bacterial Activity of Compound
Having Formula IV, Nadifloxacin, Ofloxacin, and
Sparfloxacin Against Some Gram-Negative Bacteria

| | $MIC_{90}$ (µg/ml) | | | |
| --- | --- | --- | --- | --- |
| Strain | Compound Having Formula IV | Nadifloxacin | Ofloxacin | Sparfloxacin |
| *Escherichia coli* (O-1) | 0.1 | 0.2 | 0.05 | 0.012 |
| *Klebsiella pneumoniae* (IFO 13541) | 0.024 | 0.1 | 0.024 | 0.012 |
| *Salmonella typhimurium* (TD) | 0.05 | 0.2 | 0.05 | 0.012 |
| *Shigella flexneri* (2b) | 0.006 | 0.006 | 0.006 | 0.006 |

TABLE 2-continued

Comparison of In vitro Anti-bacterial Activity of Compound Having Formula IV, Nadifloxacin, Ofloxacin, and Sparfloxacin Against Some Gram-Negative Bacteria

| Strain | MIC$_{90}$ (μg/ml) | | | |
|---|---|---|---|---|
|  | Compound Having Formula IV | Nadifloxacin | Ofloxacin | Sparfloxacin |
| *Enterobacter aerogenes* (IFO 13534) | 0.39 | 1.56 | 0.2 | 0.1 |
| *Serratia marcenscens* (NHL) | 0.2 | 1.56 | 0.1 | 0.2 |
| *Proteus mirabilis* (IFO 13300) | 0.1 | 0.1 | 0.05 | 0.1 |
| Proteus rettgeri | 0.39 | 0.39 | 0.2 | 0.2 |
| *Acinetobacter calcoaceticus* (IFO 12552) | 0.39 | 0.78 | 0.39 | 0.024 |
| *Pseudomonas aeruginosa* (IFO 13736) | 1.56 | 3.13 | 1.56 | 0.78 |
| *Pseudomonas aeruginosa* (ATCC 27853) | 1.56 | 6.25 | 3.13 | 0.78 |

Anti-bacterial activity of the compound having Formula IV was tested against several Gram-positive reference bacteria strains and compared to the anti-bacterial activity of three commercially available antibiotics (nadifloxacin, ofloxacin, and sparfloxacin). The results are shown in Table 3 as MIC$_{90}$ values.

TABLE 3

Comparison of In vitro Anti-bacterial Activity of Compound Having Formula IV, Nadifloxacin, Ofloxacin, and Sparfloxacin Against Some Gram-Positive Bacteria

| Strain | MIC$_{90}$ (μg/mL) | | | |
|---|---|---|---|---|
|  | Compound Having Formula N | Nadifloxacin | Ofloxacin | Sparfloxacin |
| *Bacillis subtilis* (ATCC 6633) | 0.012 | 0.006 | 0.05 | 0.024 |
| *Staphylococcus aureus* (ATCC 25933) | 0.05 | 0.05 | 0.39 | 0.1 |
| *Staphylococcus aureus* (FDA 209P) | 0.012 | 0.024 | 0.2 | 0.024 |
| *Staphylococcus aureus* (Smith) | 0.006 | 0.024 | 0.2 | 0.05 |
| *Staphylococcus epidermidis* (ATCC 12228) | 0.05 | 0.1 | 0.78 | 0.2 |
| *Sarcina lutea* (ATCC 9341) | 0.1 | 0.39 | 3.13 | 1.56 |
| *Streptococcus faecalis* (IFO 12964) | 0.1 | 0.78 | 1.56 | 0.78 |
| *Streptococcus faecalis* (ATCC 29212) | 0.2 | 0.78 | 1.56 | 0.39 |
| *Streptococcus pyogenes* (Cook) | 0.1 | 0.78 | 0.78 | 0.39 |
| *Streptococcus pyogenes* (IID 698) | 0.1 | 0.1 | 0.39 | 0.2 |
| *Streptococcus pneumoniae* (IID 553) | 0.1 | 0.78 | 1.56 | 0.39 |
| *Streptococcus pneniae* (IID 554) | 0.2 | 0.78 | 1.56 | 0.39 |

Anti-bacterial activity of the compound having Formula IV was tested against some methicillin-resistant *Staphylococcus aureus* bacteria strains and compared to the anti-bacterial activity of three commercially available antibiotics (nadifloxacin, ofloxacin, and sparfloxacin). The results are shown in Table 4 as MIC$_{90}$ values.

TABLE 4

Comparison of In vitro Anti-bacterial Activity of Compound Having Formula IV, Nadifloxacin, Ofloxacin, and Sparfloxacin Against Some Methicillin-Resistant *Staphylococcus aureus* Isolates

| Strain | MIC$_{90}$ (μg/mL) | | | |
|---|---|---|---|---|
|  | Compound Having Formula IV | Nadifloxacin | Ofloxacin | Sparfloxacin |
| *Staphylococcus aureus* (ATCC 33591) | 0.012 | 0.006 | 0.05 | 0.024 |
| *Staphylococcus aureus* (ATCC 33592) | 0.05 | 0.05 | 0.39 | 0.1 |
| *Staphylococcus aureus* (ATCC 33593) | 0.012 | 0.024 | 0.2 | 0.024 |
| *Staphylococcus aureus* (No. 395) | 0.006 | 0.024 | 0.2 | 0.05 |
| *Staphylococcus aureus* (No. 415) | 0.05 | 0.1 | 0.78 | 0.2 |
| *Staphylococcus aureus* (No. 419) | 0.1 | 0.39 | 3.13 | 1.56 |
| *Staphylococcus aureus* (No. 420) | 0.1 | 0.78 | 1.56 | 0.78 |
| *Staphylococcus aureus* (No. 421) | 0.2 | 0.78 | 1.56 | 0.39 |

Anti-bacterial activity of the compound having Formula IV was tested against selected anaerobic reference bacteria and compared to the anti-bacterial activity of three commercially available antibiotics (nadifloxacin, ofloxacin, and sparfloxacin). The results are shown in Table 5 as MIC$_{90}$ values.

TABLE 5

Comparison of In vitro Anti-bacterial Activity of Compound Having Formula IV, Nadifloxacin, Ofloxacin, and Sparfloxacin Against Some Common Anaerobic Bacteria

| | $MIC_{90}$ (μg/mL) | | | |
|---|---|---|---|---|
| Strain | Compound Having Formula IV | Nadifloxacin | Ofloxacin | Sparfloxacin |
| Clostridium perfringens (KZ 210) | 0.2 | 0.2 | 0.78 | 0.39 |
| Peptostreptococcus micros (GIFU 7824) | 0.2 | 0.39 | 0.78 | 0.78 |
| Peptostreptococcus magnum (GAI 0664) | 0.05 | 0.2 | 0.39 | 0.1 |
| Propionibacterium acnes (GAI 5419) | 0.2 | 0.2 | 0.78 | 0.39 |
| Propionibacterium acnes (ATCC 6919) | 0.2 | 0.2 | 0.78 | 0.39 |
| Propionibacterium acnes (ATCC 11828) | 0.39 | 0.78 | 1.56 | 0.78 |
| Bacteroides fragillis (GAI 0675) | 0.1 | 1.56 | 1.56 | 0.78 |
| Bacteroides thetaiotaomicron (GAI 0659) | 0.2 | 1.56 | 3.13 | 0.78 |
| Bacteroides vulgatus (GAI 0673) | 0.1 | 0.78 | 3.13 | 0.78 |
| Veillonella parvula (GAI 5602) | 0.1 | 0.78 | 0.39 | 0.2 |

Anti-bacterial activity of the compound having Formula IV was tested against some ophthalmologic clinical bacteria isolates and compared to the anti-bacterial activity of three commercially available antibiotics (nadifloxacin, ofloxacin, and ciprofloxacin). As disclosed above, most of these bacteria strains are also relevant to infections of the ear and upper respiratory tract. The results are shown in Table 6 as $MIC_{90}$ values.

TABLE 6

Comparison of In vitro Anti-bacterial Activity of Compound Having Formula IV, Nadifloxacin, Ofloxacin, and Ciprofloxacin Against Some Clinical Bacteria Isolates

| | $MIC_{90}$ (μg/mL) | | | |
|---|---|---|---|---|
| Strain | Compound Having Formula IV | Norfloxacin | Ofloxacin | Ciprofloxacin |
| Gram-negative | | | | |
| Moraxella species | 0.13 | 0.25 | 0.13 | ≦0.06 |
| Pseudomonas aeruginosa | 4 | 4 | 4 | 0.5 |
| Haemophilus influenzae | ≦0.06 | ≦0.06 | ≦0.06 | ≦0.06 |
| Gram-positive | | | | |
| Staphylococcus aureus | 1 | >128 | 32 | 64 |
| Coagulase-negative Staphylococcus | 0.5 | 128 | 8 | 16 |
| Streptococcus pneumoniae | 0.13 | 8 | 2 | 1 |
| Corynebacterium species | 2 | 16 | 32 | 8 |
| Propionibacterium acnes | 0.25 | 4 | 1 | 0.5 |

TABLE 6-continued

Comparison of In vitro Anti-bacterial Activity of Compound Having Formula IV, Nadifloxacin, Ofloxacin, and Ciprofloxacin Against Some Clinical Bacteria Isolates

| | $MIC_{90}$ (μg/mL) | | | |
|---|---|---|---|---|
| Strain | Compound Having Formula IV | Norfloxacin | Ofloxacin | Ciprofloxacin |
| Antibiotic-resistant Organisms | | | | |
| Ofloxacin-resistant Enterobacteriaceae | 16 | 128 | 64 | 32 |
| Ofloxacin-resistant Staphylococcus aureus | 8 | >128 | >128 | >128 |
| Gentamycin-resistant Staphylococcus aureus | 4 | 128 | 128 | 128 |
| Gentamycin-resistant Pseudomonas aeruginosa | 32 | 128 | 64 | 32 |
| Penicillin-resistant Streptococcus pneumoniae | 0.13 | 8 | 2 | 1 |

The results show that the compound having Formula IV is effective against bacteria, including some antibiotic-resistant strains, which have been found in cases of infection of the eye, ear, or upper respiratory tract. Although the applicants do not wish to be bound by any particular theory, they believe that the unique moieties on the fluoroquinolones disclosed herein provide their advantageous antibacterial property and are effective for the treatment, reduction, amelioration, or prevention of infection of the ear, including otitis externa and otitis media, and infection of the upper respiratory tract, including sinusitis, nasopharyngitis, and oropharyngitis.

The following examples are provided to further illustrate non-limiting compositions of the present invention, and methods of preparing such composition, for the treatment, reduction, amelioration, or prevention of infections.

EXAMPLE 1

Antibacterial Solution

| Ingredient | Amount (% by weight) |
|---|---|
| Compound having Formula IV | 0.2 |
| Tobramycin | 0.3 |
| Hydroxypropylmethyl cellulose ("HPMC") | 0.5 |
| Benzakonium chloride ("BAK") | 0.01 |
| Pluronic ® F127 | 0.1 |
| EDTA | 0.1 |
| NaCl | 0.25 |
| Phosphate buffer (0.05M, pH = 5.0) | q.s. to 100 |

An appropriate proportion (shown in the above table) of Pluronic® F127 is added to phosphate buffer in a sterilized stainless steel jacketed vessel equipped with a stirring mechanism, at a temperature in the range from 50 to 60° C. The resulting buffer solution is heated to 61 to 75° C. At a temperature of about 66° C., an appropriate amount of BAK is added to the buffer solution while mixing three to ten minutes. At a temperature of 75° C., appropriate amounts of the compound having Formula IV and tobramycin are added to the contents of the vessel over a period of three to fifteen minutes while mixing continues. EDTA and NaCl are then added to the mixture while mixing continues for five to fifteen more minutes at 75° C. The resulting mixture is cooled to 25 to 30° C. The final composition is packaged in appropriate containers.

EXAMPLE 2

Antibacterial Solution

A procedure similar to that of Example 1 is used to produce this solution.

| Ingredient | Amount (% by weight) |
|---|---|
| Compound having Formula IV | 0.35 |
| Trimethoprim | 0.3 |
| Mannitol | 4.5 |
| Benzakonium chloride ("BAK") | 0.005 |
| Polysorbate 80 | 0.1 |
| EDTA | 0.05 |
| Sodium acetate | 0.03 |
| Acetic acid | 0.04 |
| Purified water | q.s. to 100 |

EXAMPLE 3

Antibacterial and Anti-Inflammatory Solution

A procedure similar to that of Example 1 is used to produce this solution having the following composition.

| Ingredient | Amount (% by weight) |
|---|---|
| Compound having Formula IV | 0.2 |
| Neomycin | 0.25 |
| Dexamethasone | 0.1 |
| Hydroxypropylmethyl cellulose ("HPMC") | 0.5 |
| Alexidine | 0.01 |
| Brij ® surfactant | 0.1 |
| EDTA | 0.1 |
| Citrate buffer (0.02M sodium citrate, pH = 5) | q.s. to 100 |

EXAMPLE 4

Antibacterial, Anti-Fungal, and Anti-Inflammatory Solution

A procedure similar to that of Example 1 is used to produce this solution having the following composition.

| Ingredient | Amount (% by weight) |
|---|---|
| Compound 8 of Table 1 | 0.3 |
| Chlormidazole | 0.2 |
| Colecoxib | 0.15 |
| Propylene glycol | 0.5 |
| Alexidine | 0.01 |
| Tyloxapol | 0.1 |
| EDTA | 0.1 |
| Citrate buffer (0.02M sodium citrate, pH = 5) | q.s. to 100 |

EXAMPLE 5

Antibacterial, Antiviral, and Anti-Inflammatory Suspension

A procedure similar to that of Example 1 is used to produce this solution having the following composition.

| Ingredient | Amount (% by weight) |
|---|---|
| Compound having Formula VI | 0.3 |
| Rifampin | 0.25 |
| Triamcinolone, micronized USP | 0.2 |
| Hydroxyethyl cellulose | 0.25 |
| BAK | 0.01 |
| Tyloxapol | 0.05 |
| EDTA | 0.01 |
| NaCl | 0.3 |
| $Na_2SO_4$ | 1.2 |
| Sulfuric acid and/or NaOH | q.s. for pH adjustment to 5.5 |
| Citrate buffer (0.02 M sodium citrate, pH = 5) | q.s. to 100 |

EXAMPLE 6

Antibacterial and Anti-Inflammatory Emulsion

A modification of the procedure of Example 1 is used to produce this emulsion having the composition shown in the table immediately below.

Polysorbate 60 (Tween 60) is added to water in a first sterilized stainless steel jacketed vessel, equipped with a stirring mechanism, at a temperature of 50° C. to 60° C. in amounts corresponding the proportions shown in the table below. The resulting aqueous solution is heated to 61° C. to 75° C. At a temperature of 66° C., benzyl alcohol (a preservative) is added to the aqueous solution while mixing three to ten minutes. At a temperature of 75° C., appropriate amounts of the compound having Formula IV and loteprednole etabonate are added to Mygliol oil in a second sterilized vessel, also equipped with a stirring mechanism, over a period of three to five minutes while stirring continues. Sorbitan monostearate and cetyl stearyl alcohol are added to the oil mixture. The resulting oil mixture is heated to a temperature in the range from 62° C. to 75° C. The oil mixture is then added with vigorous mixing to the aqueous solution in the first vessel at a temperature of 66° C. over a period of three to five minutes. Sodium sulfate and sulfuric acid and/or sodium hydroxide are added to the mixture to adjust pH to 5.5. The resulting composition is cooled to 35° C. to 45° C. and homogenized by mixing with a high shear emulsifier or running through a homogenizer. The composition is further cooled to 25° C. to 30° C. The final composition is packaged in appropriate containers.

| Ingredient | Amount (% by weight) |
|---|---|
| Compound having Formula IV | 0.5 |
| Loteprednol etabonate | 0.2 |
| Polysorbate 60 | 1 |
| Sorbitan monostearate (an emulsifier) | 1.5 |
| Cetyl stearyl alcohol (an emulsion stabilizer) | 1.5 |
| Benzyl alcohol | 0.5 |
| Miglyol oil | 14.5 |
| $Na_2SO_4$ | 1.2 |

-continued

| Ingredient | Amount (% by weight) |
| --- | --- |
| Sulfuric acid and/or NaOH | q.s. for pH adjustment to 5.5 |
| Purified water | q.s. to 100 |

Typically, the oil used in an emulsion is a non-irritating emollient oil. Illustrative but non-limiting examples thereof include a mineral oil, vegetable oil, and a reformed vegetable oil of known composition. More specific but non-limiting examples of the oil can be selected from the group consisting of peanut oil, sesame seed oil, cottonseed oil, and a medium chain ($C_6$ to $C_{12}$) triglycerides (e.g., Miglyol Neutral Oils 810, 812, 818, 829, 840, etc., available from Huls America Inc.). Typical emulsifiers employed can be selected from the group consisting of sorbitan monostearate and Tween 60 (also known as Polysorbate 60). Preferably, the emulsifiers are nonionic. The emulsifiers can be employed in an amount of 1.5 to 6.5% by weight of the composition, and preferably, 3 to 5% by weight of the composition. The hydrophobic phase of the emulsion can be in an amount of 15 to 25% by weight of the composition, and preferably, 18 to 22% by weight of the composition.

EXAMPLE 7

Antibacterial, Antifungal, and Anti-Inflammatory Emulsion

A procedure similar to that of Example 6 is used to produce this emulsion having the following composition.

| Ingredient | Amount (% by weight) |
| --- | --- |
| Compound 13 of Table 1 | 0.5 |
| Butoconazole | 0.2 |
| Triamcinolone, micronized USP | 0.2 |
| Polysorbate 60 | 1 |
| Sorbitan monostearate | 1.5 |
| Cetyl stearyl alcohol | 1.5 |
| Benzyl alcohol | 0.5 |
| Miglyol oil | 14.5 |
| Na$_2$SO$_4$ | 1.2 |
| Sulfuric acid and/or NaOH | q.s. for pH adjustment to 5.5 |
| Purified water | q.s. to 100 |

EXAMPLE 8

Antibacterial Ointment

A procedure similar to that of Example 1 is used to produce this solution having the following composition.

| Ingredient | Amount (% by weight) |
| --- | --- |
| Compound having Formula VI | 0.3 |
| Apramycin | 0.2 |
| White petrolatum USP | 50 |
| Propylene glycol | 5 |
| Glycerin | 5 |
| Tween ® 20 | 2 |
| Vitamin E | 1 |
| BAK | 0.1 |
| Mineral oil | q.s. to 100 |

EXAMPLE 9

Antibacterial and Anti-Inflammatory Ointment

A procedure similar to that of Example 1 is used to produce this solution having the following composition.

| Ingredient | Amount (% by weight) |
| --- | --- |
| Compound having Formula IV | 0.3 |
| Gatifloxacin | 0.1 |
| Dexamethasone | 0.15 |
| White petrolatum USP | 50 |
| Propylene glycol | 5 |
| Glycerin | 5 |
| Tween ® 20 | 2 |
| Vitamin E | 1 |
| Vitamin D | 0.5 |
| BAK | 0.1 |
| Mineral oil | q.s. to 100 |

EXAMPLE 10

Antibacterial and Antiviral Solution

A procedure similar to that of Example 1 is used to produce this solution.

| Ingredient | Amount (% by weight) |
| --- | --- |
| Compound having Formula IV | 0.35 |
| Mannitol | 4.5 |
| Adenine arabinoside | 0.3 |
| Benzakonium chloride ("BAK") | 0.005 |
| Polysorbate 80 | 0.1 |
| EDTA | 0.05 |
| Sodium acetate | 0.03 |
| Acetic acid | 0.04 |
| Purified water | q.s. to 100 |

EXAMPLE 11

Antibacterial and Antifungal Solution

A procedure similar to that of Example 1 is used to produce this solution.

| Ingredient | Amount (% by weight) |
| --- | --- |
| Compound having Formula IV | 0.2 |
| Compound having Formula VI | 0.2 |
| Amphotericin B | 0.3 |
| Mannitol | 4.5 |
| Benzakonium chloride ("BAK") | 0.005 |
| Polysorbate 80 | 0.1 |
| EDTA | 0.05 |
| Sodium acetate | 0.03 |
| Acetic acid | 0.04 |
| Purified water | q.s. to 100 |

EXAMPLE 12

Antibacterial Emulsion

The procedure of Example 6 is used to produce this emulsion having the composition shown in the table immediately below.

| Ingredient | Amount (% by weight) |
| --- | --- |
| Compound having Formula IV | 0.5 |
| Moxifloxacin | 0.2 |
| Polysorbate 60 | 1 |
| Sorbitan monostearate (an emulsifier) | 1.5 |
| Cetyl stearyl alcohol (an emulsion stabilizer) | 1.5 |
| Benzyl alcohol | 0.5 |
| Miglyol oil | 14.5 |
| $Na_2SO_4$ | 1.2 |
| Sulfuric acid and/or NaOH | q.s. for pH adjustment to 5.5 |
| Purified water | q.s. to 100 |

EXAMPLE 13

Antibacterial Composition Comprising Compound Having Formula IV and Ciprofloxacin Compositions having various combinations of concentrations of compound having Formula IV and cirprofloxacin were tested systematically against *S. aureus*, *P. aeruginosa*, and *E. coli*. The MICs (in μg/ml) of each drug alone and in combination are shown in Table 7.

TABLE 7

MICs of Compound Having Formula IV and Ciprofloxacin Alone and in Combination

| Organism | Compound Having Formula IV Alone | Ciprofloxacin Alone | Compound Having Formula IV in Combination | Ciprofloxacin in Combination |
| --- | --- | --- | --- | --- |
| S. aureus (ATCC 29213) | 0.03 | 0.5 | 0.015 | 0.25 |
|  |  |  | 0.0005-0.001 | 0.5 |
| P. aeruginosa (ATCC 27853) | 4 | 0.5 | 1 | 0.25 |
|  |  |  | 1-2 | 0.012 |
|  |  |  | 2 | 0.06 |
| E. coli (ATCC 25922) | 0.12 | 0.015-0.030 | ≦0.03 | 0.015 |
|  |  |  | 0.015-0.06 | 0.008 |
|  |  |  | 0.03-0.06 | 0.004 |
|  |  |  | 0.03-0.06 | 0.002 |
|  |  |  | 0.015-0.03 | 0.008 |
|  |  |  | 0.06 | 0.004 |

Data of Table 7 show that although ciprofloxacin alone is effective against *S. aureus*, combinations of the compound having Formula IV and ciprofloxacin can be more effective than either drug alone against *P. aeruginosa* and *E. coli* as MIC of at least one drug in the combination is less than one-half that of the same drug used alone.

The present invention also provides a method for treating, reducing, ameliorating, or preventing infection of the eye, ear, or upper respiratory tract. In one aspect, such an infection is caused by mixed types of microorganisms including at least a bacterium. In another aspect, said at least a bacterium is one that is resistant to at least a commonly used antibiotic. In still another aspect, the method comprises administering one or more drops of a composition of the present invention to the ear canal, nasal cavity, or back of the throat of a subject who has indication of infection or whose risk of infection is indicated. A composition of the present invention can also be formulated into a spray, which can be administered into the otic or nasal cavity of such a subject.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. A method for treating, reducing, or ameliorating a bacterial infection in a subject, the method comprising administering to a subject in need thereof, a synergistic composition comprising: (a) a fluoroquinolone having Formula IV or salts thereof; and (b) ciprofloxacin; wherein Formula IV is

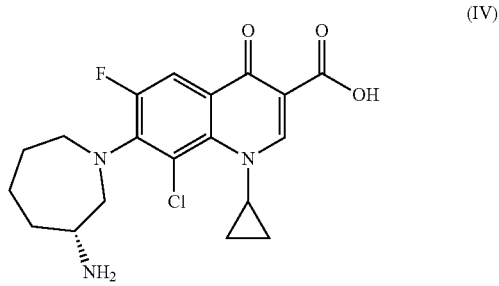

(IV)

and wherein each of the compound having Formula IV and ciprofloxacin is present in the composition at a concentration in the range from 0.0001% to 10% by weight of the composition.

2. The method of claim 1, wherein the composition is administered topically, orally, or systemically.

3. The method of claim 2, wherein the composition is administered topically.

4. The method of claim 3, wherein the infection is an infection of an eye, an ear, a portion of a respiratory system, or a combination thereof.

5. The method of claim 1, wherein the composition further comprises an additional anti-infective agent selected from the group consisting of antiviral agents, antifungal agents, antiprotozoal agents, antibacterial agents other than the fluoroquinolone having Formula IV and ciprofloxacin, and combinations thereof.

6. The method of claim 5, wherein said infection is caused by a bacterium and a fungus, and said additional anti-infective agent is an antifungal drug.

7. The method of claim 5, wherein said infection is caused by a bacterium and a virus, and said additional anti-infective agent is an antiviral drug.

8. The method of claim 5, wherein said infection is caused by a bacterium and a protozoa, and said additional anti-infective agent is an antiprotozoal drug.

* * * * *